United States Patent [19]

Sutton et al.

[11] Patent Number: 5,200,462
[45] Date of Patent: Apr. 6, 1993

[54] SUCCINIMIDE CONTAINING POLYMERS AND LATTICES PREPARED FROM SAME

[75] Inventors: Richard C. Sutton, Rochester; Ignazio S. Ponticello, Pittsford; Susan J. Danielson; Marsha D. B. Oenick, both of Rochester, all of N.Y.

[73] Assignee: Eastman Kodak Company, Rochester, N.Y.

[21] Appl. No.: 646,132

[22] Filed: Jan. 25, 1991

[51] Int. Cl.$^5$ .................. C08L 39/00; C08F 122/40; C08F 212/06

[52] U.S. Cl. .......................... 524/548; 526/262; 526/347

[58] Field of Search .......................... 524/548

[56] References Cited

U.S. PATENT DOCUMENTS

| | | | |
|---|---|---|---|
| 3,857,931 | 12/1974 | Hager | 424/12 |
| 4,138,383 | 2/1979 | Rembaum et al. | 260/29.7 |
| 4,181,636 | 1/1980 | Fischer | 260/8 |
| 4,264,766 | 4/1981 | Fischer | 536/51 |
| 4,278,651 | 7/1981 | Hales | 424/1 |
| 4,323,644 | 4/1982 | Nakamura et al. | 430/518 |
| 4,451,569 | 5/1984 | Kobayashi et al. | 435/188 |
| 4,710,525 | 12/1987 | Kraemer et al. | 523/201 |
| 4,914,210 | 4/1990 | Levenson et al. | 548/413 |
| 4,921,654 | 5/1990 | Hou et al. | 264/45.5 |
| 5,030,697 | 7/1991 | Hugl et al. | 525/326.9 |

*Primary Examiner*—Joseph L. Schofer
*Assistant Examiner*—Wu C. Cheng
*Attorney, Agent, or Firm*—Judith A. Roesler

[57] ABSTRACT

Water-insoluble, noncrosslinking, nonporous copolymers are provided which have recurring units derived from:

(a) from 0 to about 99.9 mole percent of one or more ethylenically unsaturated polymerizable oleophillic monomers which provide hydrophobicity to said copolymer, provided that none of said monomers are crosslinking monomers, (b) from about 0.1 to 100 mole percent of one or more ethylenically unsaturated polymerizable monomers having a succinimidoxycarbonyl group, and (c) from 0 to about 10 mole percent of one or more ionic or polar hydrophilic ethylenically unsaturated polymerizable monomers. These copolymers have a variety of uses, including diagnostic assays.

11 Claims, No Drawings

SUCCINIMIDE CONTAINING POLYMERS AND LATTICES PREPARED FROM SAME

RELATED APPLICATION

Reference is made to copending and commonly assigned U.S. Ser. No. 646,303, filed on even date herewith by Sutton, Ponticello, Danielson, and Oenick and entitled "Method of Preparing Biologically Active Reagents from Succinimide-Containing Polymers, Analytical Element and Methods of Use".

FIELD OF THE INVENTION

This invention relates to succinimidoxycarbonyl group-containing copolymers. The copolymers have a variety of uses, including their use in diagnostic methods and analytical elements, which are described in more detail in U.S. Ser. No. 646,303, noted above.

BACKGROUND OF THE INVENTION

There is a continuing need in various research and industrial arts for polymerizable monomers which can be polymerized into useful copolymers. For example, for photographic elements, there is a need for crosslinking agents to harden gelatin by reaction with the amine groups on the gelatin to covalently bond the crosslinking agent to the gelatin.

Moreover, there is also a continuing need in medical practice and research, and in analytical and diagnostic procedures for rapid and accurate determinations of chemical and biological substances which are present in various fluids, such as biological fluids. For example, the presence of drugs, narcotics, hormones, steroids, polypeptides, metabolites, toxins, viruses, microorganisms or nucleic acids in human or animal body fluids or tissues must be determined rapidly and accurately for effective research, diagnosis or treatment.

In approximately the last twenty years, a wide variety of analytical methods have been developed to detect the substances noted above. Generally, the state of the art has advanced to such a degree that analytical and diagnostic methods have become highly reliable, and suitable for automation or for use with test kits which can be readily used in doctors' offices or at home. Most of such methods rely on what are known in the art as "specific binding" reactions in which an unknown substance to be detected (known as a "ligand") reacts specifically and preferentially with a corresponding "receptor" molecule. Most well known specific binding reactions occur between immunoreactants, such as antibodies and antigens (foreign substances which produce immunological responses).

Methods in the art using the specific binding reactions generally require that one or more of both of the reactants be immobilized on a solid substrate of some type, so that unreacted (and generally water-soluble) materials can then be separated from the water-insoluble reaction product (often called a "complex"). In addition, such immobilized reactants can be used in affinity chromatography to remove a desired biologically active material from a mixture of such materials.

U.S. Pat. No. 4,278,651 (issued Jul. 14, 1981 to Hales) relates to a supported receptor for use in an assay for a ligand in which the solid support contains a water insoluble polymer having available at least one reactive functional group which is either carboxyl, isothiocyanate, N-hydroxysuccinimide, imidazolide, bromoacetyl, maleimide or diazomethylene. The receptor is covalently linked to the support through the reactive functional group. Generally, the support is a core-shell particle having an outer porous coating as the shell which also has the necessary functional groups. The core of the particle provides structural integrity for the porous shell materials.

Acrylic, acid-based photopolymerizable compositions have been prepared which are capable of binding bioactive substances after being photopolymerized, as described in U.S. Pat. No. 4,451,569 (issued May 29, 1984 to Schneider et al). These compositions may be applied as a coating on a carrier substrate, photopolymerized and a bioactive substance fixed thereto. The composition contains acrylic acid, a photoinitiator, a photopolymerization activator and adhesion promoter, and a copolymerizable olefinic monomer which contains a reactive functional group capable of binding bioactive substances. The olefinic monomer is preferably N-hydroxysuccinimide acrylate, N-hydroxysuccinimide amidocaproate, epoxypropyl acrylate or 2-isocyanato-ethyl acrylate.

Also, biologically active substances have thus been immobilized to advantage on particulate substrates such as polymeric particles, animal and human erythrocytes, bacterial cells and other materials known in the art. In some cases, the particulate substrates are fashioned or chemically treated to provide reactive groups on their outer surfaces for appropriate reaction with the biological substance. If the particulate substrate is a polymeric material, it often can be prepared from monomers having the appropriate reactive groups.

For example, carboxylated latex particles have been used to prepare diagnostic reagents, as noted in U.S. Pat. No. 4,181,636 (issued Jan. 1, 1980 to Fischer). The described particles are prepared using a carboxyl-containing monomer such as acrylic acid, methacrylic acid, itaconic acid, aconitic acid, fumaric acid or maleic acid. Similar particles are described in U.S. Pat. No. 3,857,931 (issued Dec. 31, 1974 to Hager), U.S. Pat. No. 4,138,383 (issued Feb. 6, 1979 to Rembaum et al) and U.S. Pat. No. 4,264,766 (issued Apr. 28, 1981 to Fischer).

The reduction of non-specific protein adsorption on polymeric surfaces has been a common goal for many workers trying to apply polymer technology to in vivo and in vitro uses in biotechnology. Undesired non-specific protein adsorption has been a continual problem. For example, nonspecific adsorption is a major concern in the use of polymers for affinity chromatography for the purification of proteins. In assays, nonspecific absorption causes unwanted background and obscures true results.

The modification of polymer surfaces has taken many forms, including physical coatings, graft copolymerization, chemical treatments and plasma gas discharge treatment. The hydrophilic nature of the polymer surface has been the subject of considerable debate and research because an increase in hydrophilicity reduces adsorption of some proteins, but not others. As noted in the art cited above, the use of reactive side chains has also received considerable attention in the art.

For example, U.S. Pat. No. 4,710,525 (issued Dec. 1, 1987 to Kraemer) relates to certain polymer particles dispersible to form a latex, to latices of such polymer particles, and to methods for immobilizing (that is, bonding or fixing) a biologically active substance on such particles. These particles have a core-shell construction and comprise groups in the shell region suitable for covalent fixation thereto of a biologically active substance. The shell is also hydrophilic and crosslinked.

Two known monomers, N-acryloyloxysuccinimide and N-(6-methacrylamidohexanoyloxy)succinimide, have been polymerized to form polymers.

Other useful monomers are listed in British Application No. 8035126, published on Jun. 17, 1981, which relates to silver halide photographic materials containing a reactive polymer having a pendant active ester group. This application lists monomers having an active ester group which can be polymerized by known methods to form the photographic materials to which this application is directed. The polymers also have the capability of being used as a crosslinked latex.

Notwithstanding the current state of the art in medical practice and analytical and diagnostic procedures, there is a need in the industry for the novel non-crosslinked copolymers of this invention which comprise water-insoluble, non-porous particles. The copolymers of this invention have the advantages of not being swellable in water so that the activity of the "receptor", as described previously, is not compromised. Further advantages of the copolymers of this invention are that: 1) it extends away from bead surface for ready covalent attachment, 2) it does not hydrolyze before covalent attachment, 3) it reacts readily and completely to form covalent protein bonds, 4) it has good reactivity with styrene monomers, and 5) the reaction chemistry is mild and does not produce by-products that require clean-up.

There is a need in the art to find new polymers which show improvement over the standard succinimideoxycarbonyl-containing polymers, especially in the attachment of biological materials for use in research and various analytical and diagnostic procedures, and also in other arts such as photography.

More recently, however, succinimidoxycarbonyl compounds have been used for this purpose with considerable advantages, as described in related application, U.S. Ser. No. 646,303 (of Sutton, et al) previously referred to herein.

SUMMARY OF THE INVENTION

The needs in the art noted above are met with a water-insoluble, noncrosslinking, nonporous copolymer having recurring units derived from:

(a) from 0 to about 99.9 mole percent of one or more ethylenically unsaturated polymerizable oleophilic monomers which provide hydrophobicity to said copolymer, provided that none of said monomers are crosslinking monomers.

(b) from about 0.1 to 100 mole percent of one or more ethylenically unsaturated polymerizable monomers having a succinimidoxycarbonyl group, and (c) from 0 to about 10 mole percent of one or more other noncrosslinking ethylenically unsaturated polymerizable monomers.

The copolymers of this invention are useful for the preparation of biologically active reagents, and in a variety of analytical and diagnostic procedures, including the analytical elements and methods described in more detail in U.S. Ser. No. 646,303 (of Sutton, et al, noted above). The reagents can also be used in affinity chromatography, as described in the noted copending application. Moreover, the monomers useful in this invention can be used to fashion polymers useful in photographic elements as well, such as non-diffusible hardenable binders, thickeners, or gelatin hardeners.

An aqueous latex composition of this invention comprises particles, having, on at least the outer surface thereof, the water-insoluble copolymer described above, the particles being present at from about 0.5 to about 35 weight percent of the composition, and preferably at from about 1 to about 20 weight percent.

Further, a method of preparing a water-insoluble, noncrosslinked, nonporous copolymer in the absence of surfactants or protective colloidal dispersing agents, is provided wherein the method comprises emulsion polymerizing:

(a) from 0 to about 99.9 mole percent of one or more ethylenically unsaturated polymerizable oleophilic monomers which provide hydrophobicity to said copolymer, provided that none of said monomers are crosslinking monomers, (b) from about 0.1 to 100 mole percent of one or more ethylenically unsaturated polymerizable monomers having a succinimidoxycarbonyl group, and (c) from 0 to about 10 mole percent of one or more other ethylenically unsaturated polymerizable monomers.

The advantages of the copolymers of this invention are that they contain a functional comonomer which survives the polymerization process, and which will subsequently react with nucleophiles such as proteins, nucleic acids, peptides and amino acids and other amino or sulfhydryl containing materials. Also, the latex particles can be directly made without hydrolysis of the succinimidoxycarbonyl active ester group.

Further, the copolymers of the invention are hydrophobic to such degree that they receive protein well (approach and are more readily absorbed to the surface of the protein) in comparison to the ability of known copolymers to receive protein.

The copolymers are also useful in the composition of this invention which provides particles which are colloidally stable to the biological chemistries of immobilization and detection, even when coated in a web format. These particles have the additional advantages of being free of surfactants and protective colloids, nonporous, and monodisperse.

DETAILED DESCRIPTION OF THE INVENTION

The copolymers of this invention can be used in a number of industrial and commercial contexts.

Copolymers of this invention can also be used in forming particles used to produce gel-grafted matte bead layers in photographic elements, for example as in U.S. Pat. No. 4,855,219 (issued Aug. 8, 1989 to Bagchi et al). Other photographic uses of such polymers, such as polymeric gelatin hardeners, hardeneable binders or vehicles, and thickeners would also be readily apparent to a skilled worker in the art.

Preferably, the polymers of this invention are used to provide reagents for medical, analytical or diagnostic methods, as described in more detail in the copending U.S. Ser. No. 646,303 (Sutton et al, noted above). The structural advantages of the succinimidoxycarbonyl group in the essential monomers used herein are its reactivity with styrene monomers, its hydrophobicity and that is less likely to hydrolyze. Therefore, the copolymers of this invention provide important advantages over known copolymers having the same use (as noted above).

The copolymers of this invention have as an essential components recurring units derived from:

(a) from 0 to about 99.9 mole percent preferably from 80.0 to about 99.9 mole percent, more preferably from 90.0 to about 99.9 mole percent, and most preferably from 95.0 to about 99.9 mole percent, of one or more ethylenically unsaturated polymerizable oleophilic monomers which provide hydrophobicity to the copolymer, provided that none of said monomers is crosslinkable, (b) from about 0.1 to 30 mole percent, preferably from 0.1 to about 20 mole percent, more preferably from 0.1 to about 10 mole percent, and most preferably from 0.1 to about 5.0 mole percent of one or more ethylenically unsaturated polymerizable monomers having a succinimidoxycarbonyl group, and (c) from 0 to about 10 mole percent, preferably from 0 to about 5 mole percent, and more preferably from 0 to about 3 mole percent of one or more other non-crosslinking ethylenically unsaturated polymerizable monomers such as ionic or polar hydrophilic monomers.

Preferably, the copolymer comprises recurring units derived from monomer (b), as described above, which can be represented by the structure:

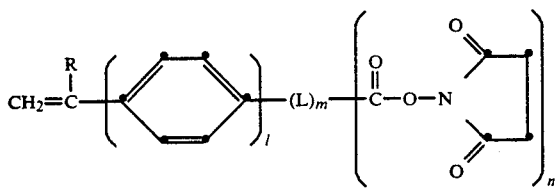

wherein:
R is hydrogen alkyl of 1 to 3 carbon atoms or halo,
L is a linking group having at least 2 carbon atoms in the linking chain wherein it consists essentially of a combination of at least two of alkylene groups having 1 to 8 carbon atoms, arylene groups having about 6 to 12 carbon atoms, hetero atoms or heteroatom-containing groups,
m is 0 or 1, n is 1 or 2, and l is 0 or 1, with the proviso that when n is 2, one of the alkylene and arylene groups is necessarily trivalent.

More specifically, in the structure noted above, R is hydrogen, alkyl of 1 to 3 carbon atoms (such as methyl, ethyl, isopropyl and n-propyl), or halo (such as chloro or bromo). Preferably, R is hydrogen, methyl or chloro. More preferably, R is hydrogen or methyl.

Also, L is an organic linking group having at least 2 carbon atoms in the linking chain and is a combination of at least two of (1) alkylene groups having 1 to 8 carbon atoms, such as methylene, ethylene or trimethylene, propylene, tetramethylene, pentamethylene, or 2,2-dimethyl-1,3-propylene, (2) arylene groups having about 6 to 12 carbon atoms, such as phenylene, tolylene, xylylene, naphthylene, and (3) divalent hetero atoms, such as oxygen (oxy), and sulfur (thio) atoms, or heteroatom-containing groups, such as carbonyl, sulfonyl, imino, ureylene, (—N'R where R is hydrogen or lower alkyl of 1 to 6 carbon atoms, such as methyl, ethyl, propyl, butyl, pentyl and hexyl).

The alkylene groups can have from 1 to 8 carbon atoms, and can be branched, linear or cyclical, substituted or unsubstituted with one or more alkyl groups (preferably of from 1 to 8 carbon atoms, such as methyl, ethyl, isopropyl, hexyl and octyl), alkoxy (preferably from 1 to 12 carbon atoms, such as methoxy, ethoxy, propoxy, t-butoxy and octyloxy), cycloalkyl (preferably from 4 to 6 carbon atoms, such as cyclobutyl, cyclo- hexyl and cyclopentyl), aryl (preferably from 6 to 12 carbon atoms, such as phenyl, tolyl, xylyl, naphthyl, 4-methoxyphenyl and chlorophenyl). Such groups are not difficult to design or synthesize for one skilled in synthetic chemistry. The arylene groups can have from about 6 to 12 carbon atoms in the aromatic nucleus, and can have the same substituents as described above for said alkylene groups.

Preferably, L comprises alkyleneoxycarbonylalkylene, alkylenethioalkyleneoxycarbonylalkylene, alkyleneimonocarbonylalkylene, iminoalkyleneoxycarbonylalkylene, alkylenethioalkylene, alkylenethioalkyleneiminocarbonylalkyleneoxyalkylene, alkylenethioalkylidyne, alkylenethioalkyleneiminocarbonylalkylenethioalkylene, alkylenethioalkyleneiminocarbonylalkylene, alkylenethioarylene, alkylenethioalkyleneoxyalkylenethioalkyleneoxycarbonylalkylene, alkyleneoxyarylenealkylenethioalkylene, alkylenethioalkyleneoxyalkylenethioalkyleneoxycarbonylalkylene, alkyleneoxyarylenealkylenethioarylenealkylenethioalkylene, alkylenethioalkyleneoxyalkylenethioalkyleneoxycarbonylarylene, carbonyloxyalkyleneoxycarbonylalkylene, carbonyloxyalkyleneureylenealkylene, carbonyloxyalkyleneiminocarbonylalkylene and carbonyloxyalkyleneoxycarbonylalkylene.

Preferably, l is 1 and L is alkylenethioalkylene, ethylenethiophenylene, or alkylenethiophenylidyne.

Representative L groups include: methyleneoxycarbonyltrimethylene, methylenethioethyleneoxycarbonyltrimethylene, methyleneiminocarbonyltrimethylene, methylene-N-methyliminoethyleneoxycarbonyltrimethylene, methylenethioethylene, methylenethioethyleneiminocarbonylmethyleneoxymethylene, methylenethio-1,1,2-ethylidynemethylenethioethyleneiminocarbonylmethylenethiomethylene, methylenethioethyleneiminocarbonyltrimethylene, methylenethio-1-carboxyethylene, methylenethiophenylene, methylenethioethyleneoxyethylenethiomethyleneoxycarbonylethylene, methyleneoxyphenylenemethylenethioethylene, methylenethioethyleneoxyethylenethioethyleneoxycarbonylethylene, methyleneoxyphenylenemethylenethiophenylenemethylenethiotrimethylene and methylenethioethyleneoxyethylenethioethyleneoxycarbonylphenylene.

Also, m is 0 or 1, n is 1 or 2, and l is 0 or 1, with the proviso that when n is 2, one of said alkylene and arylene is necessarily trivalent.

Most preferably, l and m are 0.

Preferably, monomer (b) is styrene or a styrene derivative, or an acrylic or methacrylic acid ester. More preferably, N-acryloyloxysuccinimide, 4-(2-succinimidoxycarbonylethylthiomethyl)styrene, 4-[1,2-bis(succinimidoxycarbonyl)ethylthiomethyl]styrene, or 4-(2-succinimidoxycarbonylphenylthiomethyl)styrene.

While the monomers (b) described above can be polymerized to form homopolymers, preferably they are used to prepare copolymers with one or more additional ethylenically unsaturated polymerizable monomers. For instance, the oleophilic monomers identified above as (a) monomers are useful for providing hydrophobicity or water-insoluble properties to the resulting copolymer. A mixture of such monomers can be used if desired. Such monomers would include, but not be limited to, vinyl aromatics (for example, styrene and styrene derivatives such as 4-vinyltoluene, α-methylstyrene, 2,5-dimethylstyrene, 4-t-butylstyrene and 2-chlorostyrene), acrylic and methacrylic acid esters and amides (for example, methyl acrylate, methyl methacrylate, n-butyl acrylate, 2-ethylhexyl methacrylate, benzyl acrylate and N-phenylacrylamide), butadiene, acrylonitrile, vinyl acetate, vinylbenzyl acetate, vinyl bromide, and vinylidene chloride and others readily apparent to one skilled in the art.

In addition, ethylenically unsaturated polymerizable monomers (c) other than those described above for monomers (a) or (b) can be copolymerized to provide desirable properties. For example, such monomers include anionic monomers containing sulfonic acid groups or salts thereof, including 2-acrylamido-2-methylpropane sulfonic acid, 3-methacryloyloxypropane-1-sulfonic acid, p-styrene sulfonic acid and salts thereof, and others readily apparent to one skilled in the art. Also included in the (c) group of monomers are nonionic hydrophilic monomers such as acrylamide, methacrylamide, N-isopropylacrylamide, 2-hydroxyethyl acrylate, 2-hydroxyethyl methacrylate, pentaethylene glycol monomethacrylate, N-vinyl-2-pyrrolidone and others readily apparent to one skilled in the art. In addition, monomers having active methylene groups, such as 2-acetoacetoxyethyl methacrylate, could be used, as well as many others too numerous to mention here. A skilled polymer chemist would be able to readily fashion useful polymers from hundreds of available or producible monomers using the teaching present herein.

The copolymers of this invention are water insoluble. The monomers useful in the method of making the copolymers of this invention polymerize readily with styrene. Styrene has a low solubility in water.

The method of this invention involves the preparation of a water-insoluble, noncrosslinked, nonporous copolymer in the absence of surfactants or protective colloidal dispersing agents, wherein the method comprises emulsion polymerizing:

(a) from 0 to about 99.9 mole percent of one or more ethylenically unsaturated polymerizable oleophilic monomers which provide hydrophobicity to said copolymer, provided that none of said monomers are crosslinking monomers, (b) from about 0.1 to 100 mole percent of one or more ethylenically unsaturated polymerizable monomers having a succinimidoxycarbonyl group, and (c) from 0 to about 10 mole percent of one or more other ethylenically unsaturated polymerizable monomers.

The copolymers of this invention are prepared using standard emulsion or suspension polymerization techniques, as described for example by Sorenson et al in *Preparative Methods of Polymer Science*, 2nd Ed. (1968), Wiley and Sons, New York, and by Stevens, *Polymer Chemistry, An Introduction*, Addison Wesley Publishing Co., London, 1975, although there are certain preferred conditions which are discussed below.

During polymerization, poragens (pore-producing substance) or inert diluents are not used. If used, they would normally result in the formation of pores. If porosity was required and pore integrity were to be maintained, the particles would typically have to be crosslinked so that they would not dissolve in the polymerization solvent or the inert diluent or poragen. Therefore, the particles of this invention are non-porous and do not require a crosslinked structure to be useful.

Suspension polymerization procedures are well known and generally involve mechanically dispersing the monomers in a liquid, usually water, and polymerizing the monomer droplets formed from the dispersing action. Polymerization initiators which are soluble in the monomer are generally used, and surfactants can also be used. Small particles of polymer are obtained with careful control of the polymerization conditions, which particles can be isolated using filtration, centrifugation or spray drying.

The copolymers of this invention are preferably prepared using emulsion polymerization techniques. In emulsion polymerization (whether batch, continuous or semi-continuous modes as known in the art), it is preferred that the copolymers be prepared as small particles without the use of surfactants (also known as emulsifiers) or protective colloidal dispersing agents because residual surfactant or dispersing agent on the particles tend to interfere with attachment of biologically active substances (for example, antibodies and enzymes). Thus, the resulting latex is substantially free of surfactants and colloidal dispersing agents. Conditions for surfactant-free polymerization are known in the art, for example as described in U.S. Pat. No. 4,415,700 (noted above) and *Research Disclosure* publication 15963 (July, 1977). Continuous polymerization is the most preferred technique whereby monomers are added to a reaction vessel over a period of time, as described in more detail in the noted *Research Disclosure* publication.

Some general conditions for emulsion polymerization include reaction of the monomers in the presence of water-soluble, free radical polymerization initiators (such as redox combinations of persulfates and bisulfites including potassium persulfate, ammonium persulfate, potassium bisulfite and sodium bisulfite and others known in the art) in an amount of from about 0.1 to about 5 weight % over a period of from about 30 to about 1200 minutes at a temperature of from about 30° to about 95° C. Other conditions include the use of chain transfer agents such as dodecanethiol at concentrations of from about 0.05 to about 5% (based on monomer weight).

A representative preparation of copolymers useful in this invention is provided in Example 1 below. Representative preparations of monomers useful in this invention are provided in Examples 2–4 below.

Certain preferred copolymers of this invention are generally provided in small particulate form (latices, predominantly spherical) having an average diameter of from about 0.01 to about 20 $\mu$m. Preferably, the particles have an average diameter of from about 0.01 to about 10 $\mu$m, and more preferably from about 0.1 to about 0.05 $\mu$m. The water-insoluble particles are generally nonporous and nonswellable in water or water-miscible solvents (such as alcohols), but they are also generally water-dispersible due to their small size. Polymerization procedures generally provide from about 0.5 to about 50 percent solids of copolymer, although, the latex composition of this invention generally has from about 0.5 to about 25 (preferably from about 1 to about 20) percent solids of copolymer particles when used.

Representative copolymers of this invention include, but are not limited to: poly(styrene-co-4-(2-succinimidoxycarbonylethylthiomethyl)styrene) (mole ratio 96.5:3.5), poly(styrene-co-4-[1,2-bis(succinimidoxycarbonyl)ethylthiomethyl]styrene) (mole ratio 97.5:2.5).

While in most cases, the polymers of this invention are homogeneous particles, that is, the particles are composed of the same polymer throughout, it is essential that at least the outer surface of polymeric particles be composed of a polymer of this invention. Particles having an outer shell of the polymer can be prepared by graft copolymerization of other known procedures whereby an already formed particle is coated with another polymer. Core shell polymers can be prepared, for example as described in EP-A-0 280 556 (published Sep. 12, 1990).

The following examples are provided to illustrate, and not to limit, the scope of this invention. The starting materials are commercially available unless otherwise noted. All percentages are by weight unless otherwise indicated.

EXAMPLE 1

Preparation of poly(styrene-co-N-acryloyloxysuccinimide) (96.83/3.17 molar ratio or 95/5 weight ratio)

A suitable three-neck flask (1275 ml) completely filled with distilled water was used as the reaction vessel. At 80° C., three chemical streams were simultaneously pumped into the flask. These three chemical streams comprised the following materials:

Stream 1 (monomer mix)-styrene, 765.70 g; N-acryloyloxysuccinimide, 40.73 g; dodecylmercaptan or 1-dodocanethiol, 8.06 g.

Stream 2 (oxidant)-water, distilled, 1349.91 ml, $(NH_4)_2S_2O_8$, 16.13 g.

Stream 3 (reductant)-water, distilled, 1349.91 ml, $Na_2S_2O_5$, 8.06 g. The pump rates were:

| Stream # | Rate, g/min | Rate, ml/min |
|---|---|---|
| 1 | 2.48 | 2.73 |
| 2 | 4.14 | 4.14 |
| 3 | 3.99 | 3.99 |

The theoretical solids based on flow are 23%, and the actual residence time was 128 minutes. After an addition time of 300 minutes, the reaction was stopped yielding 1081 grams of 21.4% solids. The resulting polymer latex was dialyzed for 5 days to yield 1366 g of purified latex of 16.2%. The NMR analysis of the polymer indicated a 97:3 mole ratio of styrene/succinimide monomers incorporated in the copolymer. Elemental analysis gave carbon of 89.78% (90.15% theory) and hydrogen 7.38% (7.50% theory). The particle size was 1.0 μm with a standard deviation of 0.05.

EXAMPLE 2

Preparation of 4-(2-succinimidoxycarbonylethylthiomethyl)styrene

To a stirred solution of N-hydroxysuccinimide (7.0 g, 0.06 mole), and 3-(p-vinylbenzylthio)propionic acid (13.3 g, 0.06 mole) in chloroform (100 ml) was added N,N'-dicyclohexylcarbodiimide (12.6 g, 0.06 moles) in chloroform (50 ml) at room temperature. The mixture was stirred at room temperature and the temperature of the reaction increased to 37° C. Within 5 minutes, the by-product N,N'-dicyclohexylurea began to precipitate. The reaction was stirred at 45° C. in a hot water bath for 1 hour and stirring was continued at ambient temperature overnight. The precipitated N,N'-dicyclohexylurea was then removed by filtration and the solvent was evaporated in vacuo. To the residue was added diethyl ether (100 ml) and the mixture was kept at −16° C. overnight. The white solid was collected by filtration; m.p. 63°-68° C., yield 93%.

Anal. Calcd. for $C_{16}H_{17}NO_4S$: C, 60.17; H, 5.37; N, 4.39; S, 10.04. FOUND: C, 59.32; H, 5.35; N, 4.77; S, 9.23. $^1$H NMR (CDCl$_3$) δ2.8 (broad singlet, 8H, C$\underline{H_2}$C$\underline{H_2}$,

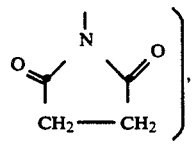

3.7 (s, 2H, ArC$\underline{H_2}$ S), 5.15 and 5.7 (AB quartet, 2H, C$\underline{H_2}$=), 6.7 (m, 1H, C$\underline{H}$=), 7.3 (m, 4H, Ar $\underline{H}$'s).

EXAMPLE 3

Preparation of 4-[1,2-Bis(succinimidoxycarbonyl)ethylthiomethyl]styrene

This compound was prepared by the same procedure described above to give a white solid, which was recrystallized from dichloromethane/ethylacetate (4:1), m.p. 118-120 with polymerization, yield 83%.

Anal. Calcd. for $C_{21}H_{20}N_2O_8S$: C, 54.78; H, 4.38; N, 6.08; S, 6.96. FOUND: C, 54.63, H, 4.41; N, 6.11; S, 7.36; $^1$H NMR (CDCl$_3$) δ2.8+2.85 (2 singlets, 8H,

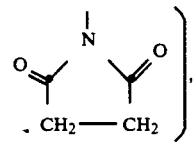

3.2 (m, 2H, C$\underline{H_2}$—CO$_2$NHS), 3.95 (t, 1H, S—C$\underline{H}$—C), 4.05 (s, 2H, C$\underline{H_2}$—S), 5.2 and 5.75 (AB quartet, 2H, C$\underline{H_2}$=), 6.7 (m, 1H, C$\underline{H}$=), 7.38 (m, 4H, Ar$\underline{H}$'s).

EXAMPLE 4

Preparation of 4-(2-succinimidoxycarbonylphenylthiomethyl)styrene

This compound was prepared by the same procedure described above to give a white solid which was crystallized from dichloromethane (100 ml)/ethyl acetate (80 ml). m.p. 155°-7° C., yield 80%.

Anal. Calcd. for $C_{20}H_{17}NO_4S$: C, 65.38; H, 4.66; N, 3.81; S, 8.73. FOUND: C, 64.91; H, 4.97; N, 3.97; S, 7.87. $^1$H NMR (CDCl$_3$) δ2.8 (s, 4H,

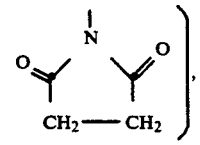

4.2 (s, 2H, C$\underline{H_2}$—S), 5.2 and 5.7 (AB quartet, 2H, C$\underline{H_2}$=), 6.65 (m, 1H, C$\underline{H}$=), 7.0-8.2 (m, 8H, Ar$\underline{H}$'s).

The invention has been described in detail with particular reference to certain preferred embodiments thereof, but it will be understood that variations and modifications can be effected within the spirit and scope of the invention. Moreover, all patents, patent applications (published or unpublished, foreign or domestic), literature references or other publications noted above are incorporated herein by reference for any disclosure pertinent to the practice of this invention.

We claim:

1. A water-insoluble, noncrosslinked, nonporous copolymer having recurring units derived from:
   (a) from 80 to about 99.9 mole percent of one or more ethylenically unsaturated polymerizable oleophilic monomers which provide hydrophobicity to said copolymer, provided that none of said monomers are crosslinking monomers,
   (b) from about 0.1 to 20 mole percent of one or more ethylenically unsaturated polymerizable monomers having a succinimidoxycarbonyl group, and
   (c) from 0 to about 10 mole percent of one or more other ethylenically unsaturated polymerizable monomers.

2. The copolymer of claim 1 having from 0 to about 5 mole percent of recurring units derived from monomer (c).

3. The copolymer of claim 1 having from about 0.1 to about 10 mole percent of recurring units derived from (b).

4. The copolymer of claim 1 wherein monomer (b) is represented by the structure:

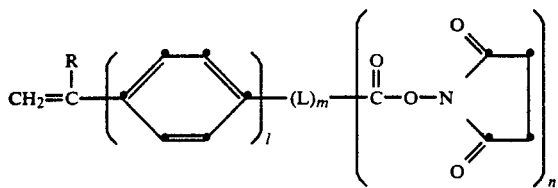

wherein:
   R is hydrogen, alkyl of 1 to 3 carbon atoms or halo,
   L is a linking group having at least 2 carbon atoms in the linking chain and is a combination of at least two of (1) alkylene groups having 1 to 8 carbon atoms, (2) arylene groups having about 6 to 12 carbon atoms, and (3) hetero atoms or heteroatom-containing groups,
   m is 0 or 1, n is 1 or 2, and l is 0 or 1, with the proviso that when n is 2, one of said alkylene and arylene is necessarily trivalent.

5. The copolymer of claim 4 wherein R is hydrogen, methyl, or chloro.

6. The copolymer of claim 4 wherein monomer (b) is N-acryloyloxysuccinimide, 4-(2-succinimidoxycarbonylethylthiomethyl)styrene, 4-[1,2-bis(succinimidoxycarbonyl)ethylthiomethyl]-styrene, or 4-(2-succinimidoxycarbonylphenylthiomethyl)styrene.

7. An aqueous latex composition comprising nonporous particles of a water-insoluble, noncrosslinked copolymer having recurring units derived from:
   (a) from 80 to about 99.9 mole percent of one or more ethylenically unsaturated polymerizable oleophilic monomers which provide hydrophobicity to said copolymer, provided that none of said monomers are crosslinking monomers,
   (b) from about 0.1 to 20 mole percent of one or more ethylenically unsaturated polymerizable monomers having a succinimidoxycarbonyl group, and
   (c) from 0 to about 10 mole percent of one or more other ethylenically unsaturated polymerizable monomers.

8. The composition of claim 7 wherein monomer (b) is represented by the structure:

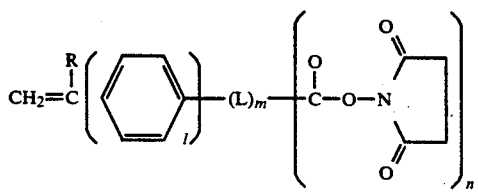

wherein:
   R is hydrogen, alkyl of 1 to 3 carbon atoms or halo,
   L is a linking group having at least 2 carbon atoms in the linking chain wherein it consists essentially of a combination of at least two of alkylene groups having 1 to 8 carbon atoms, arylene groups having about 6 to 12 carbon atoms, or hetero atoms or heteroatom-containing groups,
   l is 0 or 1, m is 0 or 1, n is 1 or 2, with the proviso that when n is 2, one of said alkylene and arylene is necessarily trivalent.

9. The composition of claim 7 wherein monomer (b) is N-acryloyloxysuccinimide, 4-(2-succinimidoxycarbonylethylthiomethyl)styrene, 4-(1,2-bis(succinimidoxycarbonyl)ethylthiomethyl)styrene, or 4-(2-succinimidoxycarbonylphenylthiomethyl)styrene.

10. The composition of claim 7 which is substantially free of surfactants and protective colloidal dispersing agents.

11. The composition of claim 7 wherein said particles have an average diameter of from about 0.01 to about 10 μm.

* * * * *